United States Patent [19]

Chocholaty et al.

[11] 4,130,126
[45] Dec. 19, 1978

[54] INK MAINTENANCE SENSOR

[75] Inventors: Warren L. Chocholaty; Robert K. Evans, both of San Jose; Francis J. Perry, Morgan Hill, all of Calif.

[73] Assignee: International Business Machines Corporation, Armonk, N.Y.

[21] Appl. No.: 801,689

[22] Filed: May 31, 1977

[51] Int. Cl.² .................................... G05D 11/06
[52] U.S. Cl. ............................... 137/3; 73/453; 137/91; 346/75
[58] Field of Search .............. 137/3, 91, 92; 73/453; 346/75

[56] References Cited

U.S. PATENT DOCUMENTS

| 3,557,817 | 1/1971 | Royse | 137/91 |
| 3,848,618 | 11/1974 | Royse | 137/91 |
| 3,952,761 | 4/1976 | Friedland | 137/91 |

Primary Examiner—Robert G. Nilson
Attorney, Agent, or Firm—Shelley M. Beckstrand

[57] ABSTRACT

Apparatus and method for detecting and correcting for evaporation from recirculated unused ink drops in an ink jet printer. The specific gravity of the recirculating ink is compared with that of a standard by measuring the time of fall of heavy floats through reservoirs of circulated and uncirculated fluid. A significant difference in fall times is compensated by the replenishment of fluid in the recirculating ink supply.

8 Claims, 4 Drawing Figures

INK MAINTENANCE SENSOR

BACKGROUND OF THE INVENTION

This invention relates generally to ink jet printing apparatus and more particularly to an automatic ink concentration measuring and fluid replenishing system for such apparatus.

DESCRIPTION OF THE PRIOR ART

Ink jet printing systems are known which pump ink from an ink reservoir to a nozzle for projection to a record medium. Unused ink is recirculated from the nozzle to the reservoir.

In such systems, adverse ink characteristic changes occur due to fluid evaporation from recirculated unused ink drops. The concentration of the ink must then be restored and maintained within appropriate tolerances, in order to assure:

1. The ink will remain in an operable range for proper ink jet operation, including stream breakoff, charging, deflection, and drop guttering.
2. The ink will have the proper concentration to achieve the printing contrast specified.
3. The ink solution will not deteriorate through increased particle count and precipitation.

One prior art attempt to detect and compensate for fluid evaporation includes measuring the resistivity of the ink. However, this has the disadvantage that the ink's resistivity has nonlinear characteristics which are affected not only by evaporative losses, but also by temperature. Consequently, temperature detection and compensation must also be provided, which adds significantly to the cost and complexity of the system.

Other prior art devices for detecting and compensating for ink fluid evaporative losses rely on the specific gravity of the solution. In one such device, a float containing a magnet is suspended in the solution. As the specific gravity of the solution changes, due to evaporation of the fluid, the float rises causing the magnet to activate a reed switch or other such transducer. In yet another such device, the float normally rests on the bottom of a chamber in a sunken position. Periodically, a coil mounted in the bottom is energized to magnetically buck the float up from the sunken position. The specific gravity of the solution determines whether the float assembly floats or sinks to the bottom, thus providing an on/off determination of the specific gravity of the fluid. In such "hydrometer" devices, the operation temperature range, batch to batch variations in the ink solution, and the accuracy of the hydrometer make it difficult to clearly define an operating point — the specific gravity above which fluid must be added to the solution in which the hydrometer floats until the specific gravity drops to a level at which the hydrometer float sinks.

SUMMARY OF THE INVENTION

It is, therefore, an object of the invention to provide a device for controlling the specific gravity of a solution.

By way of summary, the invention provides a device which measures the specific gravity of a solution by timing the fall of a heavy float through the solution a predetermined distance.

In accordance with another aspect of the invention, the change in the specific gravity of a fluid due to evaporation is determined by measuring the difference in the fall rates of two heavy floats, one through a working solution subject to evaporation, and another through a reference solution not subject to evaporation.

DESCRIPTION

Figure 1:
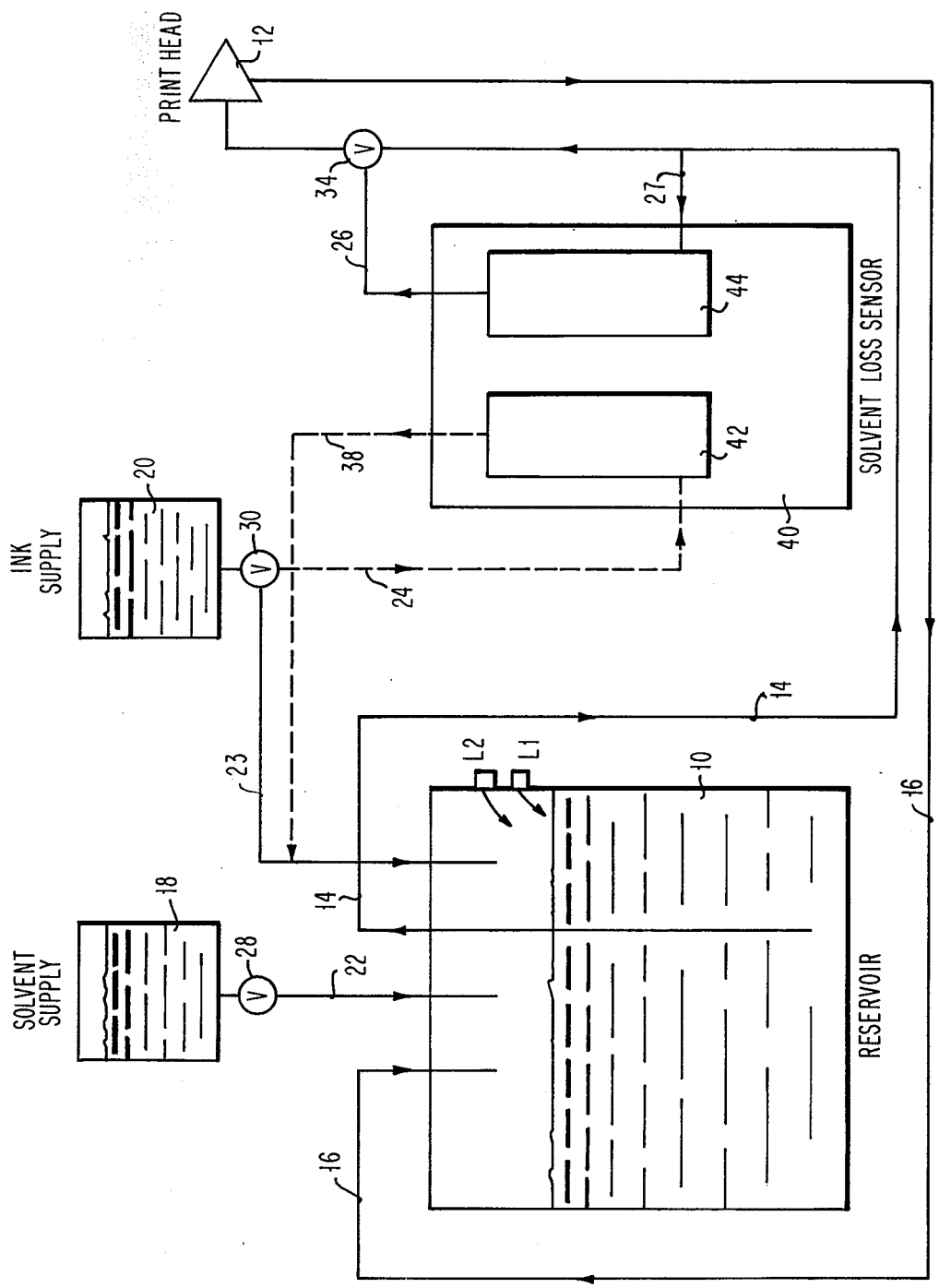
FIG. 1 is a diagrammatical representation of an ink jet printing system having the ink concentration measurement and evaporated fluid replenishment apparatus of the invention.

Referring now to the drawings, a more detailed explanation will be given of the invention. In FIG. 1, a diagrammatical representation of an ink jet printing apparatus having the specific gravity or ink concentration measurement and evaporated fluid replenishment apparatus of the invention is shown.

Ink fluid is pumped from reservoir 10 to print head 12 through pipe 14. The unused ink solution returns to reservoir 10 from print head 12 through pipe 16. The valve 34 in pipe 14 controls the passage of fluid through the print head 12 from reservoir 10 and return. As the fluid, herein water, evaporates from reservoir 10 or print head 12, it is replenished from water reservor 18 through valve 28 and pipe 22. Level indicators L1 and L2 are provided for signaling the presence of liquid at selected levels within reservoir 10.

Solvent loss sensor 40 comprises standard hydrometer unit 42 and a working fluid hydrometer unit 44. Periodically, working fluid from pipe 14 is directed into working fluid hydrometer 44 by operation of valve 34 and returned to the path to print head 12 through pipe 26. Ink supply reservoir 20 provides ink to reservoir 10 through valve 30 and pipe 23 or pipes 24 and 38. When reservoir 10 is to be replenished from reservoir 20, the fluid in reservoir 10 is emptied (not shown) and refilled through the path of pipes 24 and 38 so as to prime standard hydrometer unit 42 to contain the same fluid from the same batch as that which is fed into working fluid reservoir 10.

By another embodiment, standard hydrometer 42 may be a sealed capsule containing a reference fluid that is not changed between batches. In this case, reservoir 10 is filled directly from ink supply 20 via pipe 23. Standard hydrometer 42 and working hydrometer 44 are maintained at a constant temperature by being mounted together within unit 40, with working fluid from reservoir 44 circulated through chamber 49 (see FIG. 2). In this way, as will be more fully explained hereinafter, the evaporative losses from the fluid in reservoir 10 can be measured as a function of the differences in specific gravity between the fluids in hydrometer unit 42 and 44, with compensation for variations in temperature and from batch to batch.

Figure 2:
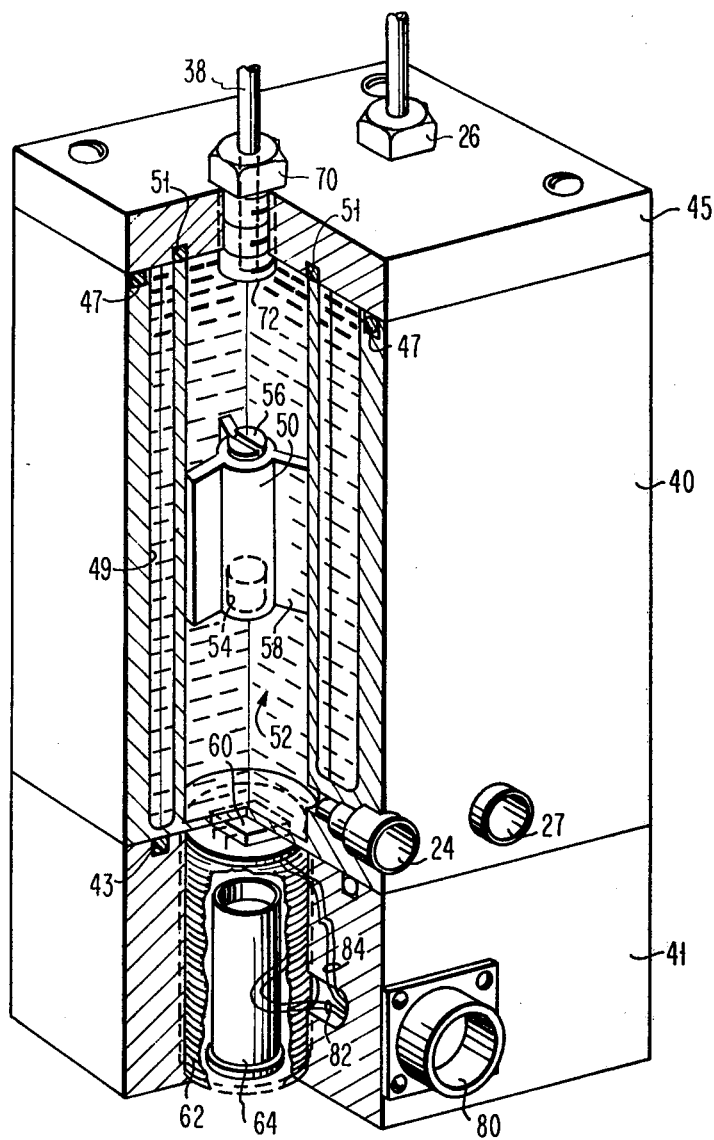
FIG. 2 is a cut away perspective view of the ink concentration measuring chamber.

Referring now to FIG. 2, a detail of the structure of fluid evaporation sensor 40, including a more detailed cut away view of hydrometer unit 42, will be explained.

In FIG. 2, fluid evaporation sensor unit 40 includes base 41 and top 45 fastened together to form reference fluid chamber 52, a similar chamber (not shown) for the working fluid hydrometer unit 44, and temperature control chamber 49. Seal 49 is provided for preventing leakage of fluid between base 41 and body 40 from the exterior environment into the coil 62 chamber. Seal 47 is provided to prevent leakage of fluid between top 45 and wall portion 40. Seal 51 is provided for preventing leakage between chambers 49 and 52. Within chamber 52, is provided heavy float unit 50. The term "heavy float" is used to designated element 50 inasmuch as buoyancy is an important force acting thereon, but it must sink in the absence of a magnetic field, as will be described hereinafter. Heavy float 50 includes permanent magnet 54 within its core, a plurality of fins 58 for maintaining equilibrium within chamber 52 such that heavy float 50 moves within a vertical plane with minimum friction between fins 58 and the side walls of chamber 52. The top of heavy float 50 comprises screw cap 56 with an O-ring seal (not shown). Heavy float 50 is assembled with ballast (not shown) in its core such that it sinks to the bottom of chamber 52 and remains there at rest in the absence of a magnetic field. Fluid from ink supply reservoir 20 is fed into the reservoir 52 through fitting 24, and is exhausted therefrom through pipe 38 that is sealed into screw 70. (In the sealed capsule embodiment previously described, fittings 24 and 38 are not required.) Screw 70 is adjustable vertically so as to move the bottom stop surface 72. Beneath the bottom of chamber 52 is positioned Hall effect sensor 60, coil 62 and core 64. By applying a current to leads 82 from connector 80, a current is setup in coil 62 that magnetizes flux focusing core 64 in such a manner as to repulse magnet 54 and drive float 50 up against bottom surface 72 of stop screw 70. As long as energizing current is held in coil 62, float 50 is held against surface 72 at the top of chamber 52. As soon as energizing current is released from coil 62, the float 50 falls through chamber 52 until it rests on the bottom thereof, at which time Hall effect sensor 60 provides a signal along line 84 to connector 80. As will be more fully explained hereinafter, the time between release of energizing current from coil 62 and the activation of Hall effect sensor 60 by float 50 is timed to measure the specific gravity or concentration of the fluid within chamber 52.

Figure 3:
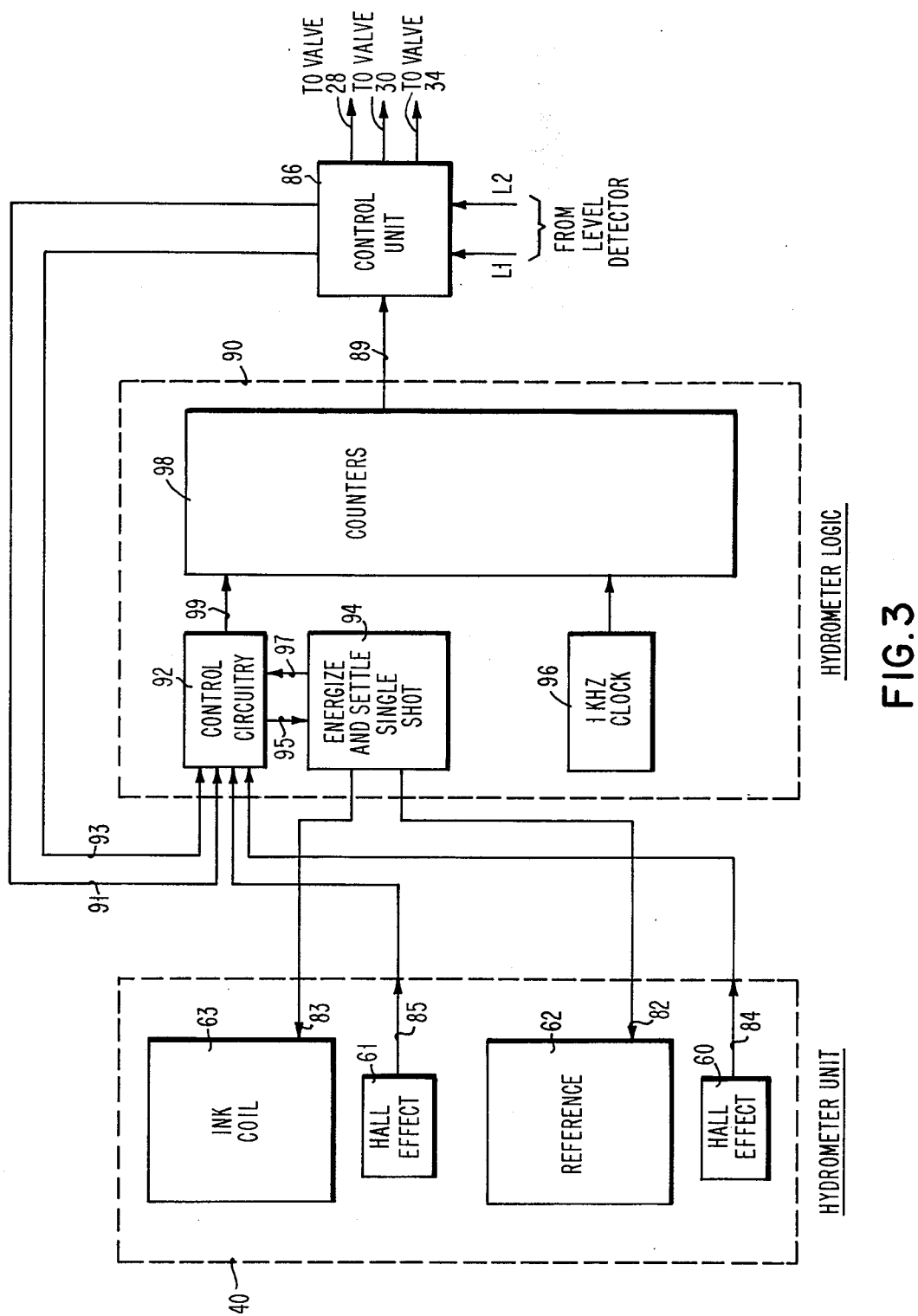
FIG. 3 is a schematic showing the hydrometer unit and concentration measuring logic.

Referring now to FIG. 3, the hydrometer control logic will be explained. Hydrometer logic 90 comprises control circuitry 92, energize and settle single shot 94, clock 96, and counter 98. Control inputs to control circuitry 92 appear on lines 91 and 93 to selectively activate measurement of the specific gravity of the reference or working fluids. Energize and settle single shot 94 is activated by a signal on line 95 to selectively energize ink coil 63 by a current on line 83, or reference coil 62 by a current in line 82. Upon expiration of the single shot, and the release of current from either coil 62 or 63, a signal to control circuitry 92 is provided on line from 97 energize and settle single shot 94. Hall effect sensors 60 and 61 provide proximity signals on lines 84 and 85, respectively, to control circuitry 92. Counter 98 is driven by clock 96, and controlled by line 99 from control circuitry 92 to count the fall time of reference float 50 or of the working fluid float (not shown) and provide a timing signal on line 89. Control unit 86 is provided for operating valve 28 to replenish the water evaporated from reservoir 10 in the event that the difference in fall times of the reference and working fluid heavy floats exceeds a predetermined valve.

In operation, a first control input on line 91 causes single shot 94 to energize reference coil 62, thereby driving heavy float 50 in hydrometer unit chamber 42 up against stop surface 72. After expiration of single shot 94, current is removed from reference coil 62 and a signal signifying such is provided on line 97. Immediately, control circuitry 92 activates counter 98 which is driven by clock 96. When float unit 50 reaches the bottom of chamber 52, a signal from Hall effect unit 60 on line 84 through control circuitry 92 and line 99 stops counter 98. Counter 98 now contains a count representing the time elapsed between the release of coil 62 and the making of Hall effect sensor 60. Next, a signal on control input 93 begins a similar process with respect to the working fluid hydrometer unit, and develops within counter 98 a count representing the time between expiration of single shot 94 and removal of energizing current from coil line 63, and the making of Hall effect sensor 61. As will be apparent to those skilled in the art, counter 98 could be operated to increment during operation of the standard hydrometer 42 and decrement during operation of the reservoir hydrometer 44 to provide on line 89 a difference value. Alternatively, line 89 could be loaded with the absolute values and control unit 86 operated to evaluate the difference and control the operation of valves 28 and 30 to compensate for fluid evaporative losses.

By another embodiment of the invention, both reference float 58 and the float in the working solution 44 may be positioned against the top of the reservoir, and then released simultaneously. The difference in fall rates is measured as the elapsed time between the generation of output signals by Hall effect transducers 60 and 61. If the transducer 61 signal follows that of transducer 62, then working solution 44 is more dense than standard solution 42. If the difference exceeds a predetermined or calculated value, then valve 28 is operated to add water to the working solution in an amount sufficient to compensate for the evaporative losses.

Figure 4:
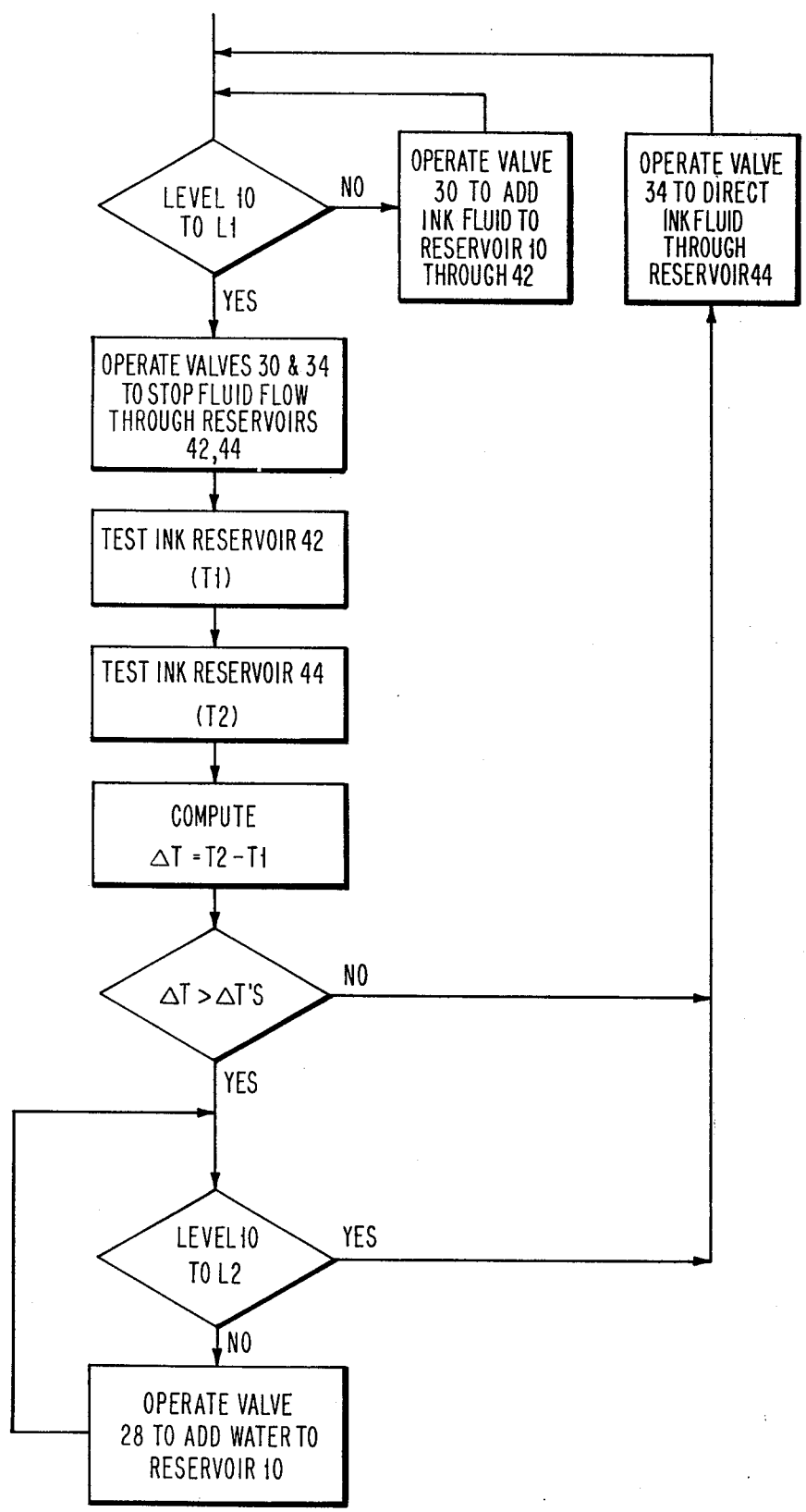
FIG. 4 is a flow chart showing the method steps of one embodiment of the invention.

Referring to FIG. 4, a flow chart of one embodiment of the method of the invention is illustrated. The process steps illustrated are controlled by control unit 86, and are as follows:

When the liquid level is reservoir 10 falls below the level of indicator L1, a signal to control unit 86 from indicator L1 causes operation of valve 30 to add ink fluid from supply 20. Periodically, say on two hour intervals, the concentration of the ink is tested and adjusted, as required, and then rechecked 15 minutes later (if adjustment was required).

When checking the ink solution concentration, valves 30 and 34 are operated to prevent fluid flow through reservoirs 42 and 44 — which flow, if permitted, may influence of cause an erroneous reading of the hydrometers.

Next, control unit 86 signals hydrometer logic 90 along lines 91 and 93 to test the concentration of ink in reservoirs 42 and 44, to compute (either in counter 98 or control unit 86) the time difference $\Delta T$ representing the difference in heavy floats fall timess T1 and T2, and therefore the difference in concentration between the reference and working fluids, respectively.

If $\Delta T$ is not greater than the reference value, $\Delta Ts$, which may be set to represent, say, a 15% water loss, then the working fluid concentration is within limits, and no adjustment is required. If $\Delta T$ exceeds $\Delta Ts$, then valve 28 is operated by control unit 86 to bring the fluid level in reservoir 10 up to level L2. Then valve 34 is operated to direct ink fluid through reservoir 44 and baffle 49 to prime hydrometer unit 44 and establish temperature equilibrium with hydrometer unit 52 for the next testing of ink concentration.

By another embodiment, the solution of reservoir 10 may be adjusted by adding water from solvent supply 18 or ink concentrate from ink supply 20. In this embodiment, valve 30 would be operated to supply ink concentrate through line 23, and lines 24 and 38 would not be required, with a sealed cartridge used for hydrometer unit 42. In this embodiment, if $T1 - T2 = \Delta T > 0$, the reference is more concentrated, and ink from supply 20 would be added to reservoir 10. On the other hand, if $T1 - T2 = \Delta T > 0$, then working fluid is the more concentrated, and solvent 18 would be added.

By a further embodiment, if $\Delta T$ is greater than some value X, which is significantly greater than the standard value, then faulty operation of valves 28, 30, or 34, or leaky fittings (permitting air in one of the hydrometer chambers) or a defective ink batch (with respect to concentration), is detected.

By a further embodiment, when the computed $\Delta T$ exceeds $\Delta T$'s, solvent 18 may be added not to bring the fluid in reservoir up to level L2, but by a specific amount metered through valve 28 according to the valve by which $\Delta T$ exceeds $\Delta T$'s. As will be apparent to those skilled in the art, a calibration curve may be derived without undue experimentation for a specific system based upon the capacity of reservoir 10, the desired ink concentration, and the measured $\Delta T$ value.

What is claimed is:

1. Apparatus for maintaining the concentration of an ink solution within predetermined limits, comprising:
    means for measuring the differential fall rates of heavy floats through said ink solution and through a reference solution;
    means responsive to said means for measuring for selectively adding ink concentrate or solvent to said ink solution to adjust the concentration of said ink solution.

2. The apparatus of claim 1, wherein said means for measuring comprises:
    a first float member including a magnetic member disposed for movement in an enclosure containing said ink solution, said first float member having a density greater than that of the ink displaced by said first float member;
    means to produce a magnetic field which interacts with said magnetic member so that said first float member is displaced to a predetermined upper position in said enclosure;
    means to measure the time required for said first float to sink to a predetermined lower position in said enclosure,
    a second float member of said density including a magnetic member disposed in an enclosure with ink of a predetermined concentration; and
    means to measure the difference in time required for said first and second float members to sink to said predetermined lower position;
    whereby change of concentration of said ink can be determined from said time difference.

3. Apparatus for controlling the concentration of an ink solution, comprising:
    means for measuring the differential fall rates of heavy floats through said ink solution and through a reference solution;
    reservoir means for holding a supply of said ink solution;
    level detector means for sensing the level of solution within said reservoir means;
    means for adding ink to said reservoir to maintain the level in said reservoir at a minimum level;
    means responsive to said differential fall rate exceeding a reference value for adding solvent to said reservoir means.

4. Apparatus for controlling the concentration of an ink solution, comprising:
    means for measuring the differential fall rate of heavy floats through said ink solution and through a reference solution;
    means for replacing the ink in said ink solution and said reference solution with new ink such that both the ink solution and reference solution are initialized with ink from a single source of ink.

5. Apparatus for compensating evaporative losses in the ink solution of an ink jet printer, comprising:
    means for measuring the differential fall rates of heavy floats through the working solution of said printer and a reference solution;
    means for altering the concentration of the working solution when said differential fall rate exceeds a predetermined value.

6. Method for changing the concentration of a fluid, comprising the steps of:
    determining the difference in the rate of fall of heavy floats in reference and working fluid solutions,
    adding fluid to the working solution when said difference exceeds a predetermined value.

7. Method for controlling the concentration of a working solution, comprising the steps of:
    measuring the differential fall rate of identical heavy floats through working and reference solutions;
    changing the concentration of the working solution when said differential fall rate exceeds a predetermined value.

8. Method for compensating for evaporative losses in the working solution of an ink jet printing device, comprising the steps of:
    measuring the fall time of a first heavy float through a first predetermined distance in a reference solution;
    measuring the fall time of a second heavy float through a second predetermined distance in said working solution;
    changing the relative concentration of the working and reference solutions when the difference in fall times exceeds a predetermined value.

* * * * *